(12) United States Patent
Sen

(10) Patent No.: US 10,998,925 B2
(45) Date of Patent: May 4, 2021

(54) WEARABLE HEALTH MONITORING SYSTEM AND METHOD USING HUMAN BODY COMMUNICATION

(71) Applicant: Purdue Research Foundation, West Lafayette, IN (US)

(72) Inventor: Shreyas Sen, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 16/412,409

(22) Filed: May 14, 2019

(65) Prior Publication Data

US 2019/0347393 A1 Nov. 14, 2019

Related U.S. Application Data

(60) Provisional application No. 62/671,102, filed on May 14, 2018.

(51) Int. Cl.
*A61B 5/00* (2006.01)
*H04B 1/10* (2006.01)
*H04W 72/08* (2009.01)
*G06F 21/32* (2013.01)

(52) U.S. Cl.
CPC .............. *H04B 1/10* (2013.01); *A61B 5/681* (2013.01); *A61B 5/683* (2013.01); *A61B 5/0028* (2013.01);
(Continued)

(58) Field of Classification Search
CPC ......... A61B 5/681; A61B 5/6812; A61B 5/68; A61B 5/6802; A61B 5/6803; A61B 5/683;
(Continued)

(56) References Cited

U.S. PATENT DOCUMENTS 6,211,799 B1 * 4/2001 Post .................... H02J 50/05
341/33
8,064,995 B1 * 11/2011 Dupelle .................. A61N 1/39
607/5
(Continued)

OTHER PUBLICATIONS

Zhao et al, A Review on Human Body Communication: Signal Propagation Model, Communication Performance, and Experimental Issues, Hindawi Wireless Communications and Mobile Computing, vol. 217, https://doi.org/10.1155/2017/5842310, pp. 1-15 (Year: 2017).*

(Continued)

*Primary Examiner* — Linda Wong
(74) *Attorney, Agent, or Firm* — Purdue Research Foundation

(57) ABSTRACT

A communication interference rejection system comprising a relatively low-impedance voltage mode driver output which receives a signal from a sensor, the sensor near a user's skin, a receiver operatively connected to a device connected to a body of a user, wherein the receiver configured to receive a signal transmitted through the body of the user. The signal comprises a relatively substantially small constant amplitude component and a relatively large sinusoidal or modulated interference component, the interference component due to human body antenna effect, the receiver comprising a high-impedance termination to minimize channel loss, the receiver further configured to receive frequencies in the 10 KHz to 10 MHz range.

4 Claims, 7 Drawing Sheets

(52) U.S. Cl.
CPC ............ *G06F 21/32* (2013.01); *H04B 1/1036* (2013.01); *H04W 72/082* (2013.01)

(58) Field of Classification Search
CPC .. A61B 5/0028; H04B 1/1036; H04W 72/082
See application file for complete search history.

(56) References Cited

U.S. PATENT DOCUMENTS

| | | | |
|---|---|---|---|
| 9,478,862 B2* | 10/2016 | Su | H01Q 5/314 |
| 10,033,106 B2* | 7/2018 | Livneh | A61B 1/00016 |
| 10,069,637 B2* | 9/2018 | Gaade | H03F 3/45085 |
| 10,644,757 B1* | 5/2020 | Kerselaers | H04B 5/0075 |
| 2017/0125892 A1* | 5/2017 | Arbabian | A61B 5/686 |
| 2018/0069712 A1* | 3/2018 | Gaade | H04L 12/10 |
| 2019/0238376 A1* | 8/2019 | Shih | H03L 7/099 |
| 2019/0313908 A1* | 10/2019 | Melodia | A61N 1/3787 |
| 2020/0028532 A1* | 1/2020 | Sen | H04B 1/123 |

OTHER PUBLICATIONS

Yang, G., et al., "The Simeck Family of Lightweight Block Ciphers," in Cryptographic Hardware and Embedded Systems CHES, pp. 307-329, 2015.

Bogdanov, A., et al., "Present: an Ultra-Lightweight Block Cipher," in Cryptographic Hardware and Embedded Systems—CHES, pp. 450-466, 2007.

Leander, G., et al., "New Lightweight DES Variants," in Fast Software Encryption, pp. 196-210, 2007.

Canniere, C., et al., "KATAN and KTANTAN—A Family of Small and Efficient Hardware-Oriented Block Ciphers," in Cryptographic Hardware and Embedded Systems—CHES 2009, Springer, pp. 272-288, 2009.

Daly, D., et al., "Through the Looking Glass—The 2017 Edition: Trends in Solid-State Circuits from ISSCC," ISSCC, 2017.

Cho, H. et al., "21.1 A 79pJ/b 80Mb/s full-duplex transceiver and a 42.5 uW 100kb/s super-regenerative transceiver for body channel communication," in ISSCC, 2015.

Zimmerman, T., "Personal Area Networks: Near-field intrabody communication," IBM Syst. J., vol. 35, No. 3.4, pp. 609-617, 1996.

Wegmueller, M., et al., "Signal Transmission by Galvanic Coupling Through the Human Body," IEEE Trans. Instrum. Meas., vol. 59, No. 4, pp. 963-969, 2010.

Sen, S., "SocialHBC: Social Networking and Secure Authentication using Interference-Robust Human Body Communication," in IEEE ISLPED 2016.

Maity, S., et al., "Adaptive Interference Rejection in Human Body Communication using Variable Duty Cycle Integrating DDR Receiver," in IEEE/ACM Design, Automation and Test in Europe 2017.

* cited by examiner

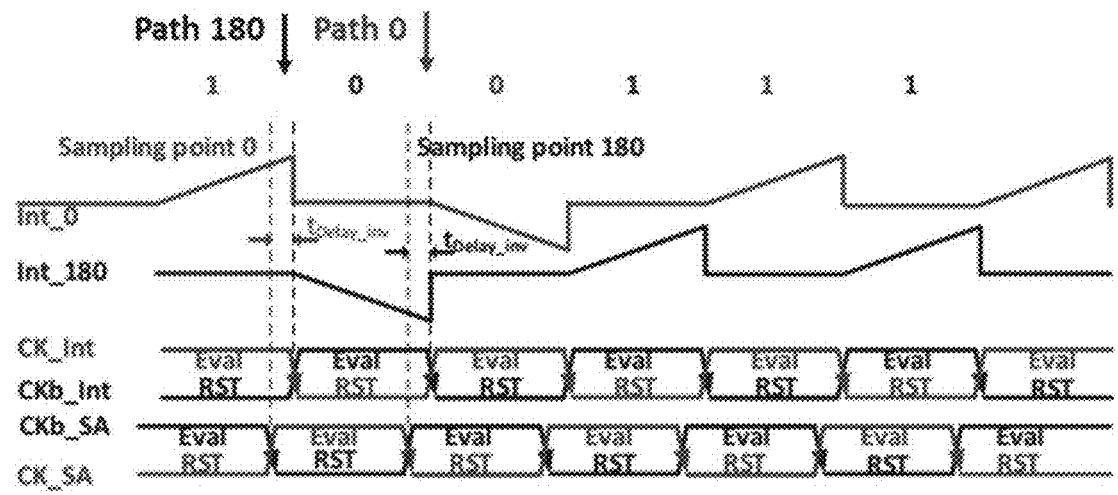
FIG. 3C
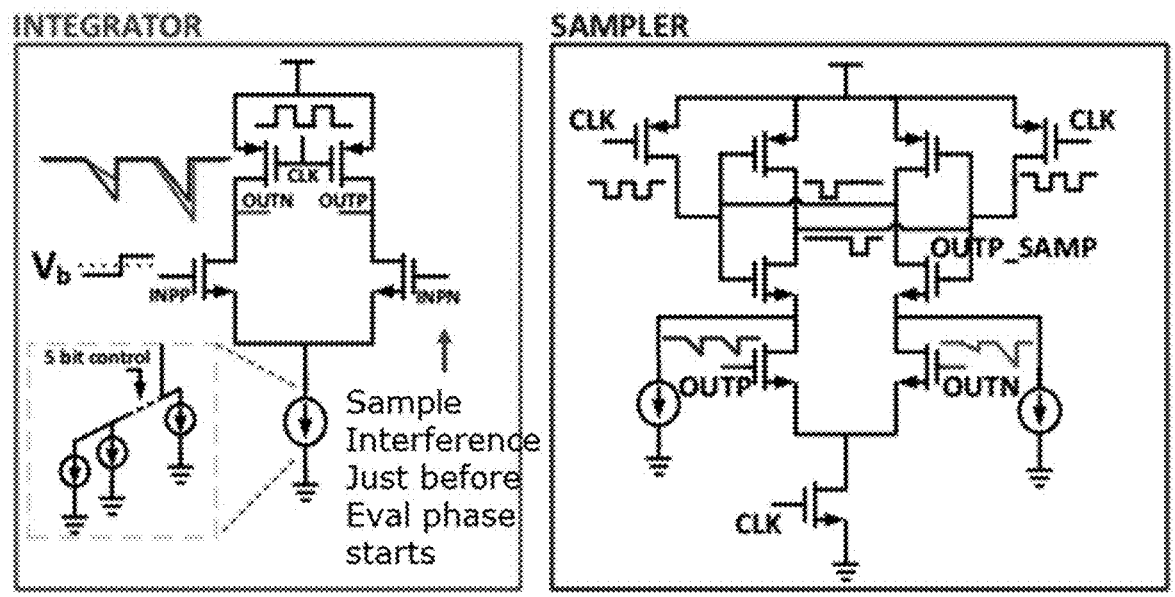
FIG. 3D  FIG. 3E

WEARABLE HEALTH MONITORING SYSTEM AND METHOD USING HUMAN BODY COMMUNICATION

CROSS REFERENCE TO RELATED APPLICATIONS

The present patent application relates to and claims the priority benefit of U.S. Provisional Application Ser. No. 62/671,102, filed May 14, 2018, the content of which is hereby incorporated herein by reference in its entirety.

TECHNICAL FIELD

The present disclosure is related to electronic communication systems, and more specifically, to electronic authentication systems which use the human body as part of a signal transmission path.

BACKGROUND

The continuous reduction of size of unit computing, has propelled the growth of wearable sensors and computing devices (e.g. Fitness trackers, Smart watches). Soon, the human body will become a platform for interconnected wearable smart devices, which will aid and improve human quality of life. This calls for efficient ways to connect these wearable devices on the human body. Moreover, since each individual will be wearing a large amount of information on their body (i.e., the Human Intranet), they can now transmit this information to other humans or machines (Human Internet) at their will or use this information for secure authentication. Such on-body wearable devices are typically interconnected using a wireless body area network (WBAN). Human Body Communication (HBC) has recently emerged as a strong contender for this human body network, as it provides ultra-low power (ULP) and increased security, compared to WBAN. ULP is achieved as human body is used as a conducting medium, which exhibits significantly lower loss than radio frequency propagation through air. HBC is more secure as the information is contained within the human body and cannot be snooped on unless the person is physically touched, unlike WBAN, where the wireless signals can be easily snooped on by an attacker.

One disadvantage of HBC is that the human body acts as an antenna at the FM frequency band. This has been the biggest bottleneck in high-speed ULP HBC implementation. Signaling techniques that allow circumvention of the interference, such as adaptive frequency hopping (AFH) and fixed narrowband signaling have been proposed. However, such systems provide no way to suppress the interference other than avoiding it using adaptive/fixed narrowband signaling, which leads to energy-inefficient implementation and requires bulky filters. Therefore, improvements are needed in the field.

BRIEF DESCRIPTION OF THE DRAWINGS

The above and other objects, features, and advantages of the present invention will become more apparent when taken in conjunction with the following description and drawings wherein identical reference numerals have been used, where possible, to designate identical features that are common to the figures, and wherein:

FIG. 2A shows an HBC system which employs capacitive voltage-mode signaling according to one embodiment.

FIG. 2B shows the associated time-domain received signals for the system of FIG. 2a.

FIG. 3C shows the associated time domain signals for the system of FIG. 3A according to one embodiment.

FIG. 3D shows the integrator circuit portion of the HBC system of FIG. 3A.

FIG. 3E shows the sampler circuit portion of the HBC system of FIG. 3A.

DETAILED DESCRIPTION

Throughout this description, some aspects are described in terms that would ordinarily be implemented as software programs. Those skilled in the art will readily recognize that the equivalent of such software can also be constructed in hardware, firmware, or micro-code. Because data-manipulation algorithms and systems are well known, the present description is directed in particular to algorithms and systems forming part of, or cooperating more directly with, systems and methods described herein. Other aspects of such algorithms and systems, and hardware or software for producing and otherwise processing signals or data involved therewith, not specifically shown or described herein, are selected from such systems, algorithms, components, and elements known in the art. Given the systems and methods as described herein, software not specifically shown, suggested, or described herein that is useful for implementation of any aspect is conventional and within the ordinary skill in such arts.

Various aspects relate to communication systems utilizing the human body as an electrical signal pathway.

The present disclosure provides an electronic communication system which utilizes capacitive voltage-mode communication or time-domain interference sampling between wearable health monitoring devices, which enables low energy, secure communication necessary for such energy constrained systems.

In view of the foregoing, various aspects provide improved reliability of an electronic communication system. A technical effect is to electronically communicate data between wearable health monitoring devices connected to the human body.

Figure 1A:
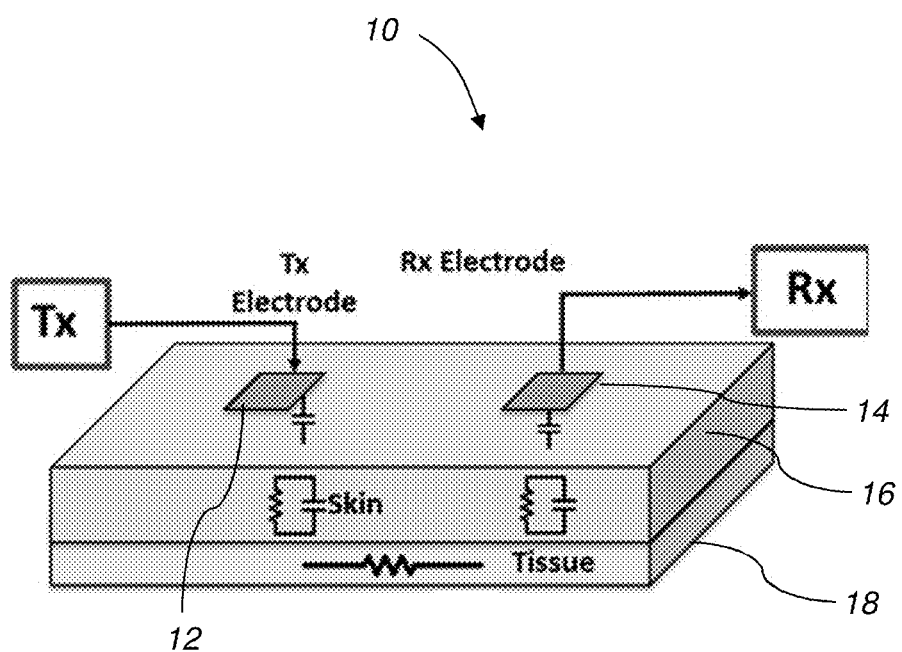
FIG. 1A shows a diagram of a human body communication system according to one embodiment.
Figure 1B:
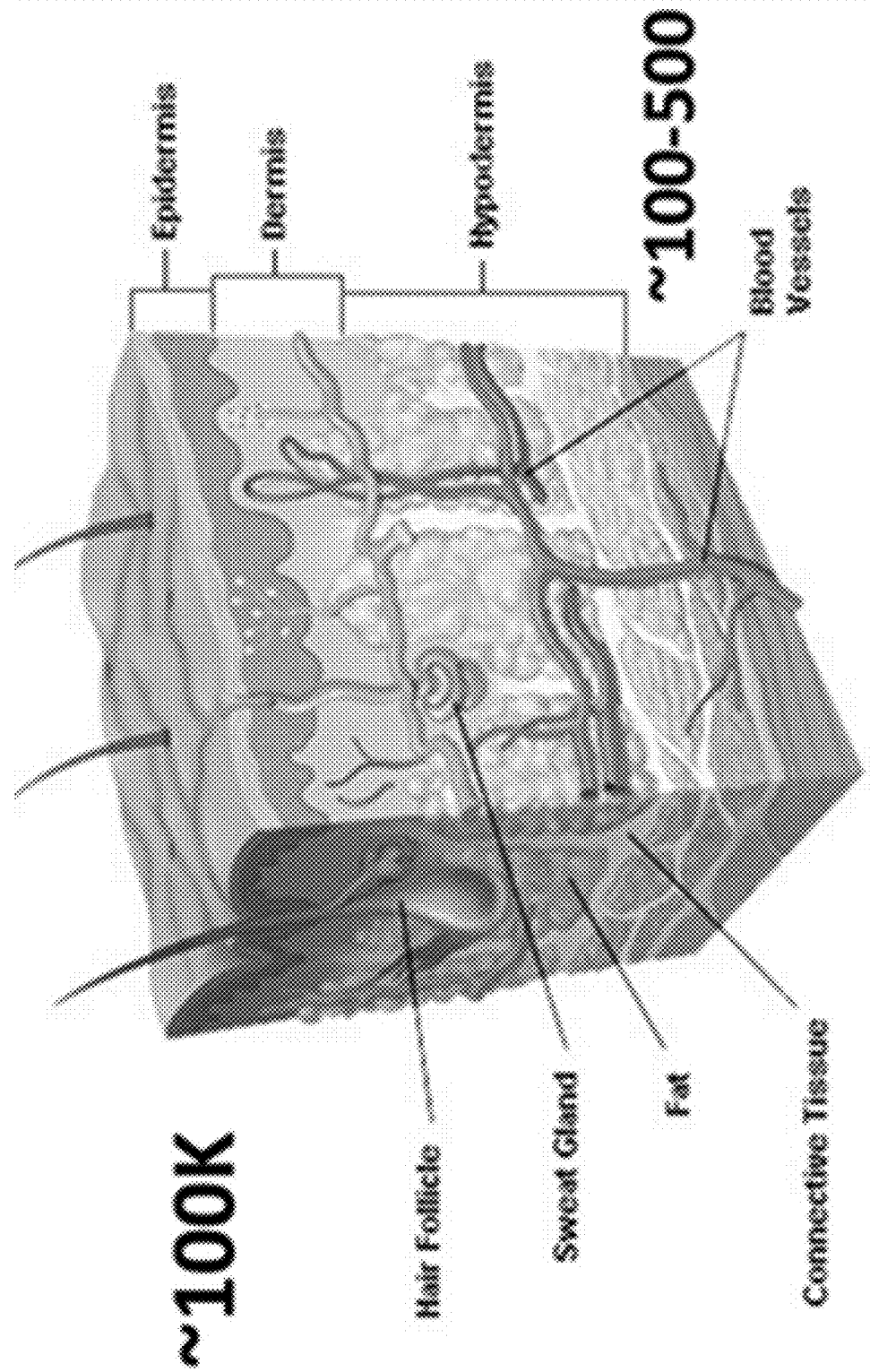
FIG. 1B shows a sample diagram of human skin and associated tissue.
Figures 1C, 1D:
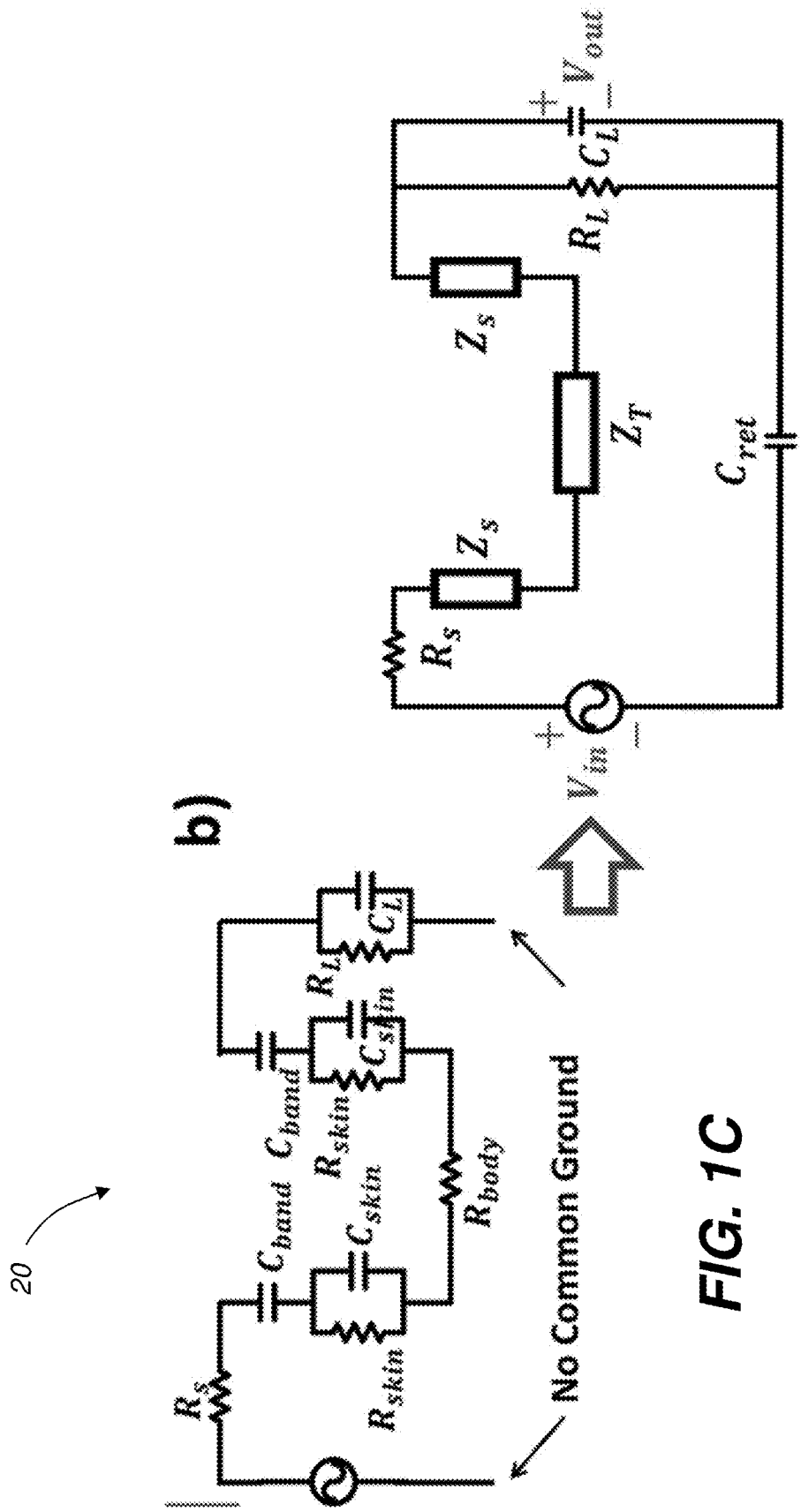
FIG. 1C shows a schematic diagram of the human body communication system of FIG. 1A according to one embodiment.
FIG. 1D shows a schematic diagram of a lumped model of the HBC system of FIG. 1a according to one embodiment.

The human body can be used as a broadband (BB) channel for data transmission. A broadband channel with ~MHz bandwidth can enable data transmission at megabits/second speed which is sufficient for applications such as image or data transfer. FIG. 1A shows a diagram of a HBC system 10 having transmit electrode 12 and receive electrode 14 adjacent or slightly separated from human skin 16, with associated lower tissue 18. FIG. 1B shows a typical human skin and tissue anatomy. FIG. 1C shows a detailed circuit diagram of a circuit 20 for capacitive HBC between two wearable devices. The circuit model 20 shows there is no common ground, meaning no closed path for current to flow. The closed path is formed using parasitic capacitances from device 1 and 2 to earth's ground (Cret), leading to the name capacitive HBC. FIG. 1D shows a simplified lumped model of a capacitive HBC between two wearable devices. $Z_S$ is a combination of the skin-electrode contact resistance and the skin tissue resistance and is in the order of KΩ. Once the signal is coupled to the body it is transferred through the low resistance tissue layers inside the body, whose impedance is modeled as $Z_T$ in FIG. 1b. The source impedance ($R_S$) is of the order of few ohms. The load could consist of a parallel combination of resistance ($R_L$), capacitance ($C_L$).

Figures 2A, 2B:
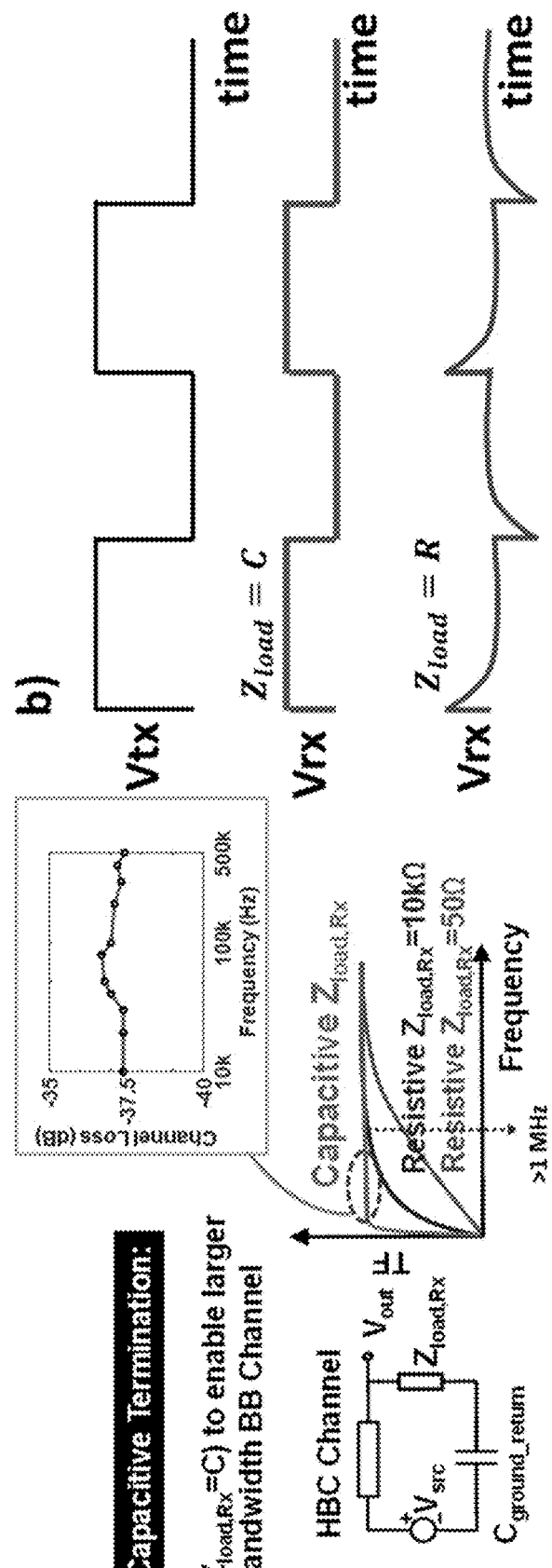

Voltage-Mode Signaling (High-Impedance Termination): Since the summation of skin and tissue impedance is above the KΩ range, a 50Ω or other low-impedance termination at the receiver creates an unfavorable voltage division, leading to a high-loss at low frequencies (FIG. 2A). The load resistance should be chosen as a high-impedance on the order of MOs (e.g. 1-10 MΩs, 1-100 MΩs or 1-900 MΩs). Efficient communication in such a scenario is achieved by focusing on the voltage transfer characteristics of the human body channel. To that end, according to one embodiment, Voltage Mode (VM) Signaling is used for the communication between the devices in the HBC system (e.g., between the sensor and a worn hub unit, or between sensors). In VM signaling, the measured metric at different points of the system is voltage and voltage transmission is achieved by a low output impedance source and a high input impedance load. In one embodiment, a signal generator is used as a low impedance source and an oscilloscope is used as a high impedance load for measurements, however, the high impedance load may comprise other devices as well.

Capacitive Voltage-Mode Signaling: FIG. 2A shows a Circuit diagram of capacitive HBC and example frequency response for capacitive termination and two cases of resistive termination. Capacitive termination allows close to flat-band response, making it suitable for broadband signaling. The closed path is formed using parasitic capacitances from device 1 and 2 to earth's ground (Cret), leading to the name capacitive HBC. Capacitive termination ($C_L$) is used at the receiver end and provides a flat-band frequency response as shown by the loss equation below:

$$\text{Channel Loss} = \frac{V_{rx}}{V_{tx}} = \frac{C_{ret}}{(C_{ret} + C_L)}$$

Since, the Channel Loss is not a function of frequency, it provides a flat-band frequency response, suitable for broadband signaling, that has energy in a broad bandwidth from DC to operating frequency. The return path is formed by a capacitance between the transmitter and the receiver. This return path capacitance and the capacitance at the receiver end forms a capacitive voltage division, as can be seen in FIG. 2A. Since a capacitive voltage division ratio is independent of frequency, this results in a channel response with almost constant loss across all frequencies, resulting in a broadband channel. A broadband channel enables transmission of a signal through the human body directly as 1/0 bits without the need of any modulation or demodulation techniques. Since the broadband HBC enables maximum utilization of available bandwidth, systems utilizing the herein described HBC system will be more power-efficient than previous narrowband wireless or HBC based systems. The time-domain response to an example broadband data stream is shown in FIG. 2B for capacitive termination and resistive termination HBC, showing the resistive termination suffers from quick signal loss with time, whereas the capacitive termination has a cleaner received signal.

Time-Domain Interference Sampling: The human body acts as an antenna and picks up interferences, which makes broadband communication through the body hard. An integrating DDR (I-DDR) receiver can handle interferences with frequency $f_{intf} = nf_{data}$, where $n$ is an positive integer Any other frequencies $f_{intf} > f_{data}$ can be rejected by dynamically adjusting the integration time $T_{int} = n*T_{intf}$, which shows that this technique works well for interferences higher than data-rate, but does not provide much benefit for interference frequencies below data-rate.

Interference frequencies below data-rate can be rejected using the following Time-Domain Interference Sampling and Subtraction (TD-ISS) technique.

Figure 3A:
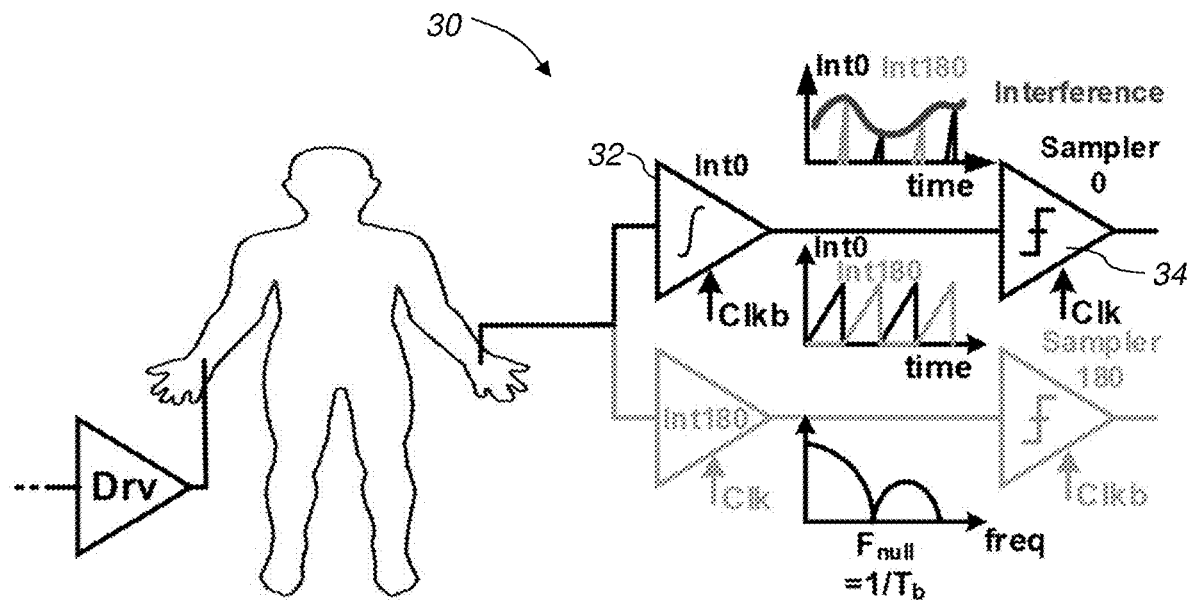
FIG. 3A shows an HBC system which employs a time-domain interference sampling and subtraction technique according to one embodiment.
Figure 3B:
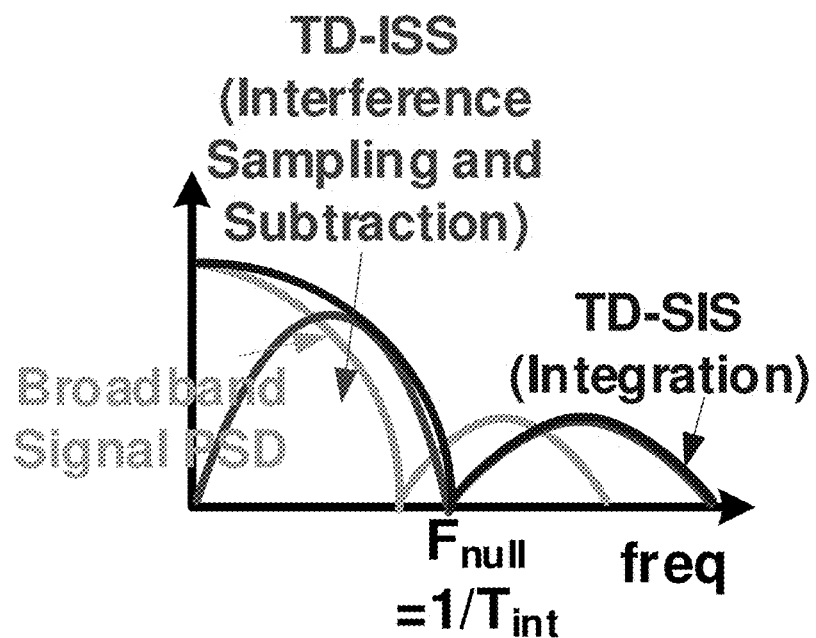
FIG. 3B shows a comparison of gain vs. frequency plots for various methods.

The details of the technique are shown in FIGS. 3A-3E. FIG. 3A shows an I-DDR receiver 30 used for interference-robust HBC signaling according to one embodiment, and the associated freq. vs. gain plot (FIG. 3B) for the two methods (TD-ISS and TD-SIS). The interference is sampled and subtracted. More specifically, the incoming signal is integrated by the integrator 32, then sampled by the sampler 34. FIG. 3C shows that the Sampling should be performed at the end of the Reset phase and the sampled value should be held on to the INPN of the integrator 32 (FIG. 3D) during the evaluation phase, leading to a subtraction of the present signal from the sampled interference at the start of the integration period. If $f_{intf} \ll f_{data}$, it can be assumed that this sampled value is constant over the bit period, canceling these interferences. FIG. 3E shows the circuit details of the sampler 34.

This way, TD-ISS provides robustness to interferences $f_{intf} < f_{data}$ (interference sampling and subtraction) and $f_{intf} > f_{data}$ (integration) simultaneously.

Steps of various methods described herein can be performed in any order except when otherwise specified, or when data from an earlier step is used in a later step. Exemplary method(s) described herein are not limited to being carried out by components particularly identified in discussions of those methods.

Figure 4:
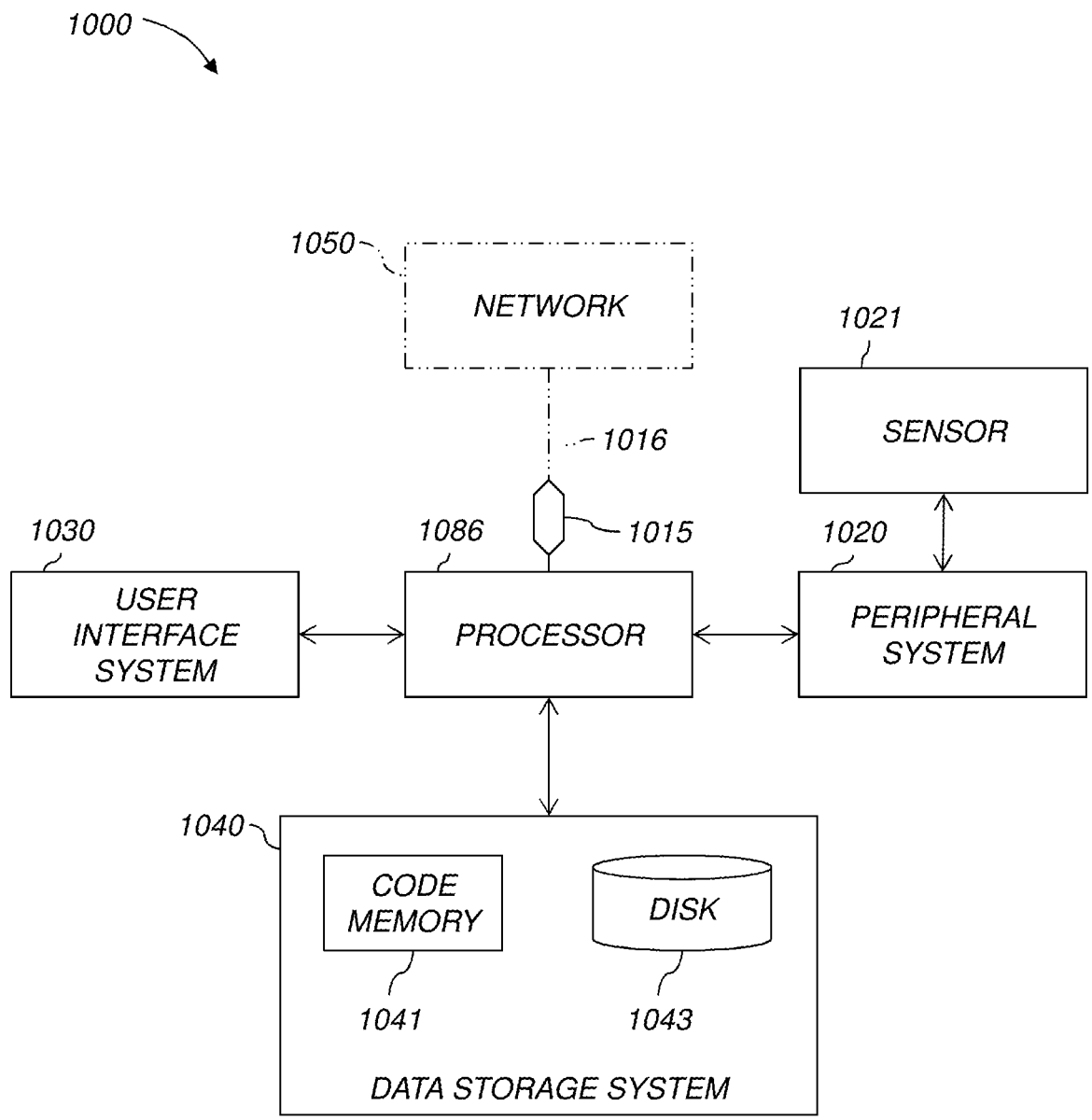
FIG. 4 shows a diagram of a data-processing system having human body communication functionality according to one embodiment.

FIG. 4 is a high-level diagram showing the components of an exemplary data-processing system 1000 for analyzing data and performing other analyses described herein, and related components. The system includes a processor 1086, a peripheral system 1020, a user interface system 1030, and a data storage system 1040. The peripheral system 1020, the user interface system 1030 and the data storage system 1040 are communicatively connected to the processor 1086. Processor 1086 can be communicatively connected to network 1050 (shown in phantom), e.g., the Internet or a leased line, as discussed below. The HBC data described herein may be received or sent through a human body via sensors 1021 (or similar transmitters) and/or displayed using display units (included in user interface system 1030) which can each include one or more of systems 1086, 1020, 1030, 1040, and can each connect to one or more network(s) 1050. Processor 1086, and other processing devices described herein, can each include one or more microprocessors, microcontrollers, field-programmable gate arrays (FPGAs), application-specific integrated circuits (ASICs), programmable logic devices (PLDs), programmable logic arrays (PLAs), programmable array logic devices (PALs), or digital signal processors (DSPs). Each of the driver circuits 14 and receivers 22 may include one or more of the processors 1086.

Processor 1086 can implement processes of various aspects described herein. Processor 1086 can be or include one or more device(s) for automatically operating on data, e.g., a central processing unit (CPU), microcontroller (MCU), desktop computer, laptop computer, mainframe computer, personal digital assistant, digital camera, cellular phone, smartphone, or any other device for processing data, managing data, or handling data, whether implemented with electrical, magnetic, optical, biological components, or otherwise. Processor 1086 can include Harvard-architecture components, modified-Harvard-architecture components, or Von-Neumann-architecture components.

The phrase "communicatively connected" includes any type of connection, wired or wireless, for communicating data between devices or processors. These devices or processors can be located in physical proximity or not. For example, subsystems such as peripheral system 1020, user interface system 1030, and data storage system 1040 are shown separately from the data processing system 1086 but can be stored completely or partially within the data processing system 1086.

The peripheral system 1020 can include one or more devices configured to provide digital content records to the processor 1086. For example, the peripheral system 1020 can include capacitive sensors 1021 or other sensors or transmitters for sending and receiving the signals described herein. The processor 1086, upon receipt of digital content records from a device in the peripheral system 1020, can store such digital content records in the data storage system 1040.

The user interface system 1030 can include a mouse, a keyboard, touchscreen, another computer (connected, e.g., via a network or a null-modem cable), or any device or combination of devices from which data is input to the processor 1086. The user interface system 1030 also can include a display device, a processor-accessible memory, or any device or combination of devices to which data is output by the processor 1086. The user interface system 1030 and the data storage system 1040 can share a processor-accessible memory.

In various aspects, processor 1086 includes or is connected to communication interface 1015 that is coupled via network link 1016 (shown in phantom) to network 1050. For example, communication interface 1015 can include an integrated services digital network (ISDN) terminal adapter or a modem to communicate data via a telephone line; a network interface to communicate data via a local-area network (LAN), e.g., an Ethernet LAN, or wide-area network (WAN); or a radio to communicate data via a wireless link, e.g., WiFi or GSM. Communication interface 1015 sends and receives electrical, electromagnetic or optical signals that carry digital or analog data streams representing various types of information across network link 1016 to network 1050. Network link 1016 can be connected to network 1050 via a switch, gateway, hub, router, or other networking device.

Processor 1086 can send messages and receive data, including program code, through network 1050, network link 1016 and communication interface 1015. For example, a server can store requested code for an application program (e.g., a JAVA applet) on a tangible non-volatile computer-readable storage medium to which it is connected. The server can retrieve the code from the medium and transmit it through network 1050 to communication interface 1015. The received code can be executed by processor 1086 as it is received, or stored in data storage system 1040 for later execution.

Data storage system 1040 can include or be communicatively connected with one or more processor-accessible memories configured to store information. The memories can be, e.g., within a chassis or as parts of a distributed system. The phrase "processor-accessible memory" is intended to include any data storage device to or from which processor 1086 can transfer data (using appropriate components of peripheral system 1020), whether volatile or nonvolatile; removable or fixed; electronic, magnetic, optical, chemical, mechanical, or otherwise. Exemplary processor-accessible memories include but are not limited to: registers, floppy disks, hard disks, tapes, bar codes, Compact Discs, DVDs, read-only memories (ROM), erasable programmable read-only memories (EPROM, EEPROM, or Flash), and random-access memories (RAMs). One of the processor-accessible memories in the data storage system 1040 can be a tangible non-transitory computer-readable storage medium, i.e., a non-transitory device or article of manufacture that participates in storing instructions that can be provided to processor 1086 for execution.

In an example, data storage system 1040 includes code memory 1041, e.g., a RAM, and disk 1043, e.g., a tangible computer-readable rotational storage device such as a hard drive. Computer program instructions are read into code memory 1041 from disk 1043. Processor 1086 then executes one or more sequences of the computer program instructions loaded into code memory 1041, as a result performing process steps described herein. In this way, processor 1086 carries out a computer implemented process. For example, steps of methods described herein, blocks of the flowchart illustrations or block diagrams herein, and combinations of those, can be implemented by computer program instructions. Code memory 1041 can also store data, or can store only code.

Various aspects described herein may be embodied as systems or methods. Accordingly, various aspects herein may take the form of an entirely hardware aspect, an entirely software aspect (including firmware, resident software, micro-code, etc.), or an aspect combining software and hardware aspects. These aspects can all generally be referred to herein as a "service," "circuit," "circuitry," "module," or "system."

Furthermore, various aspects herein may be embodied as computer program products including computer readable program code stored on a tangible non-transitory computer readable medium. Such a medium can be manufactured as is conventional for such articles, e.g., by pressing a CD-ROM. The program code includes computer program instructions that can be loaded into processor 1086 (and possibly also other processors), to cause functions, acts, or operational steps of various aspects herein to be performed by the processor 1086 (or other processor). Computer program code for carrying out operations for various aspects described herein may be written in any combination of one or more programming language(s), and can be loaded from disk 1043 into code memory 1041 for execution. The program code may execute, e.g., entirely on processor 1086, partly on processor 1086 and partly on a remote computer connected to network 1050, or entirely on the remote computer.

Various aspects are inclusive of combinations of the aspects described herein. References to "a particular aspect" (or "embodiment" or "version") and the like refer to features that are present in at least one aspect of the invention.

Separate references to "an aspect" (or "embodiment") or "particular aspects" or the like do not necessarily refer to the same aspect or aspects; however, such aspects are not mutually exclusive, unless so indicated or as are readily apparent to one of skill in the art. The use of singular or plural in referring to "method" or "methods" and the like is not limiting. The word "or" is used herein in a non-exclusive sense, unless otherwise explicitly noted.

The invention has been described in detail with particular reference to certain preferred aspects thereof, but it will be understood that variations, combinations, and modifications can be effected by a person of ordinary skill in the art within the spirit and scope of the invention.

The invention claimed is:

1. A communication interference rejection system, comprising:
   a transmitter connected to a sensor, the sensor near a user's skin; and
   a receiver having a capacitive termination, wherein a load impedance of the termination is a capacitance or a capacitance in parallel with a high resistance to achieve flat-band channel loss, the capacitive termination lowering loss at low frequencies as compared to a resistive termination;
   wherein low frequencies in the range of 10 KHz-10 MHz are used in combination with the capacitive termination and a voltage-mode communication between the transmitter and receiver to enable simultaneous low-radiation and low channel loss.

2. The system of claim 1, wherein the capacitive termination is implemented in combination with a capacitive return-path in human body communication to enable a square-wave like received signal from a square-wave like transmitted signal.

3. The system of claim 2, wherein the receiver is configured to:

a. receive a signal transmitted through the body of the user, the signal comprising receive NRZ signaling or other constant amplitude signals, the receiver comprising an integrating dual data-rate receiver;
   b. reject interference below a data rate by sampling the slowly changing interference;
   c. provide a packet structure with short no-data periods followed by long data periods;
   d. sample the slowly changing interference during the no-data period;
   e. subtract the sampled interference from subsequent received signal+interference during the data period, leading to ability to reject interferences less than data-rate in broadband human body communication systems; and
   f. apply the sampled interference to an input of an integrator of the integrating dual data-rate receiver to achieve the subtraction.

4. The system of claim 3, wherein the receiver is further configured to:

g. provide Time-domain Interference-Sampling and subtraction (TD-ISS) leading to a reduction DC and low-frequency gain in transfer function of the integrating dual data-rate receiver or rejection of low-frequency interferences;
   h. receive a signal transmitted through the body of the user, the signal comprising a relatively substantially small constant amplitude component and a relatively large sinusoidal or modulated interference component, said interference component due to human body antenna effect;
   i. integrate the signal and sample at a sampling time;
   j. sample interference just before the end of a reset period; and
   k. hold the sampled value at the non-signal input of the integrator of the integrating dual data-rate receiver.

* * * * *